(12) United States Patent
Altshuler et al.

(10) Patent No.: US 10,143,397 B2
(45) Date of Patent: Dec. 4, 2018

(54) ELECTRODE HOLDING DEVICE

(71) Applicants: Edward Lafe Altshuler, Erie, CO (US); Francis X. Palermo, Lafyette, CO (US)

(72) Inventors: Edward Lafe Altshuler, Erie, CO (US); Francis X. Palermo, Lafyette, CO (US)

( * ) Notice: Subject to any disclaimer, the term of this patent is extended or adjusted under 35 U.S.C. 154(b) by 345 days.

(21) Appl. No.: 15/183,589

(22) Filed: Jun. 15, 2016

(65) Prior Publication Data

US 2016/0360990 A1 Dec. 15, 2016

Related U.S. Application Data

(60) Provisional application No. 62/180,021, filed on Jun. 15, 2015.

(51) Int. Cl.
*A61B 5/0478* (2006.01)
*A61N 1/36* (2006.01)
*A61N 1/04* (2006.01)
*A61B 5/00* (2006.01)

(52) U.S. Cl.
CPC .......... *A61B 5/0478* (2013.01); *A61B 5/6803* (2013.01); *A61B 5/6835* (2013.01); *A61N 1/0456* (2013.01); *A61N 1/0484* (2013.01); *A61N 1/36025* (2013.01)

(58) Field of Classification Search
CPC .. A61B 5/0478; A61N 1/0526; A61N 1/0529; A61N 1/0539
USPC ........................................................ 600/383
See application file for complete search history.

(56) References Cited

U.S. PATENT DOCUMENTS

| 5,562,718 | A | | 10/1996 | Palermo | |
|---|---|---|---|---|---|
| 5,740,812 | A | * | 4/1998 | Cowan | A61B 5/0482 600/545 |
| 6,077,237 | A | * | 6/2000 | Campbell | G06F 3/011 600/587 |
| 6,154,669 | A | * | 11/2000 | Hunter | A61B 5/0478 600/383 |
| 7,483,747 | B2 | | 1/2009 | Gliner | |

(Continued)

FOREIGN PATENT DOCUMENTS

| GB | 2527157 | * | 12/2016 |
|---|---|---|---|
| WO | WO2015100499 | * | 7/2015 |

(Continued)

*Primary Examiner* — Lee S Cohen
(74) *Attorney, Agent, or Firm* — Kenneth Altshuler

(57) ABSTRACT

An electrode holding device is described using a headset having a neutral curvature with a radius smaller than a human skull. The headset adapted to provide spring load force against the human skull at the first and the second ends where first and second respective electrode holding panels are attached. The electrode holding panels conform to the human above the ears. The electrode panels are adapted to pivot about pivot points on the ends of the headset. The panels are adapted to contact the human skull under pressure from spring load force generated from the headset bent beyond the neutral curvature of the headset. The headset can in certain examples be further adapted in certain to accommodate an arm having an a third electrode panel that possesses a third electrode assembly, the third electrode assembly adapted to be spring loaded against and in contact with the human forehead.

15 Claims, 7 Drawing Sheets

(56) References Cited

U.S. PATENT DOCUMENTS

| | | | |
|---|---|---|---|
| 8,731,633 B2* | 5/2014 | Asjes | A61B 5/04085 |
| | | | 600/383 |
| 8,738,142 B2 | 5/2014 | Polermo | |
| 8,781,570 B2* | 7/2014 | Chuang | A61B 5/0478 |
| | | | 381/74 |
| 9,060,671 B2* | 6/2015 | Badower | A61B 5/00 |
| 9,788,745 B2* | 10/2017 | Hayakawa | A61B 5/0478 |
| 2004/0122303 A1* | 6/2004 | Kopke | A61B 5/0478 |
| | | | 600/383 |
| 2009/0099623 A1* | 4/2009 | Bentwich | A61N 1/36025 |
| | | | 607/45 |
| 2013/0039509 A1* | 2/2013 | Chuang | A61B 5/0478 |
| | | | 381/74 |
| 2015/0112153 A1* | 4/2015 | Nahum | A61B 5/6803 |
| | | | 600/301 |
| 2015/0164362 A1* | 6/2015 | Morrow | A61B 5/0478 |
| | | | 600/383 |

FOREIGN PATENT DOCUMENTS

| | | | |
|---|---|---|---|
| WO | WO2016070188 | * | 5/2016 |
| WO | WO2016079525 | * | 5/2016 |

* cited by examiner

ELECTRODE HOLDING DEVICE

CROSS-REFERENCE TO RELATED APPLICATIONS

This application claims priority to and the benefit of U.S. Provisional Patent Application No. 62/180,021, entitled: Electrode Holding Device, filed on Jun. 15, 2015 the entire disclosure of which is hereby incorporated by reference.

FIELD OF THE INVENTION

The present invention is directed to a device that is useful for holding electrodes in place over scalp, skull, or brain.

BACKGROUND OF THE INVENTION

Presently, there are multiple forms of surface and precutaneous neuromuscular electrical stimulation available for treatment of neurological conditions. These forms of surface and precutaneous neuromuscular electrical stimulation are used in a physician's setting and are held in place by an operator, such as a nurse, technician, or physician for example, or are set/anchored into the skull of a patient.

It is to innovations related to addressing problems with self-administering a cranial surface neuromuscular electrical stimulation outside the setting of a hospital or doctor's office that the disclosed invention is generally directed.

SUMMARY OF THE INVENTION

The present invention is directed to an electrode holding system adapted for electrical coupling between stimulating or sensing electrodes and the scalp, brain or other parts of a head. One embodiment contemplates an electrode holding system that applies directional pressure to a plurality of integrated electrodes to maintain contact on the scalp in a desired position with the target region on the scalp of a patient for either sensing electrical fields that are delivering electrical stimulation or both. Additional, embodiments contemplate at least one electrode from a channel positioned over a desired region of the brain to become activated with the assistance of the electrode holding system. Direct or alternating current can be applied transferring only to the brain at the desired location via the electrode holding system. Certain embodiments contemplate the electrode holding system essentially spring loading the electrodes via a headset device that is adapted to be positioned by the patient or user with one hand.

Another embodiment contemplates a method for using an electrode holding device comprising: providing a headset that is semi-rigid with a curvature smaller than a human skull, the headset having a first end supporting a first electrode arrangement and a second end supporting a second electrode arrangement; bending the headset in an open direction by spacing apart the first end from the second end; placing the headset over the human skull while the headset is spaced apart; releasing the headset while over the human skull allowing the first electrode and the second electrode to move towards one another in a closed position that compresses the electrodes against the human skull, the first electrode on a first panel and the second electrode on a second panel, the panels pivoting to conform to the human skull; positioning the first electrode arrangement on the human skull above a left ear and the second electrode arrangement on the human skull above a right ear; and energizing the first electrode arrangement and the second electrode arrangement while in contact with the human skull.

Other embodiments contemplate an electrode holding device comprising: a semi-rigid curved headset having a first end and a second end adapted to conform at least partially to a human skull and to provide spring load force against the human skull at the first and the second ends; a first electrode panel adapted to conform to a first portion of the human skull attached to the first end of the headset; a second electrode panel adapted to conform to a second portion of the human skull attached to the second end of the headset; the first electrode panel adapted to pivot about a first pivot point and the second electrode panel adapted to pivot about a second pivot point; a first electrode disposed in a first position on the first electrode panel arranged to contact at least part of the first portion of the human skull under pressure from the spring load force; and a second electrode disposed in a second position on the second electrode panel arranged to contact at least part of the second portion of the human skull under the pressure from the spring load force.

Yet, another embodiment contemplates an electrode holding device comprising: a headset having a neutral curvature with a radius smaller than a human skull, the headset possessing a first end and a second end adapted to conform at least partially to a human skull; the headset adapted to provide spring load force against the human skull at the first and the second ends; a first electrode panel adapted to conform to a first portion of the human skull attached to the first end of the headset above a left ear of the human skull; a second electrode panel adapted to conform to a second portion of the human skull attached to the second end of the headset above a right ear of the human skull; the first electrode panel adapted to pivot about a first pivot point and the second electrode panel adapted to pivot about a second pivot point; a first electrode assembly comprised by the first electrode panel arranged to contact at least part of the first portion of the human skull under pressure from spring load force generated from the headset bent beyond the neutral curvature; a second electrode disposed in a second position on the second electrode panel arranged to contact at least part of the second portion of the human skull under the pressure from the spring load force, and the headset adapted to accommodate an arm having an a third electrode panel that possesses a third electrode assembly, the third electrode assembly adapted to be spring loaded against and in contact with a forehead of the human skull.

DETAILED DESCRIPTION

Initially, this disclosure is by way of example only, not by limitation. Thus, although the instrumentalities described herein are for the convenience of explanation, shown and described with respect to exemplary embodiments, it will be appreciated that the principles herein may be applied equally in other types of situations involving an electrode supporting headset.

Figure 1:
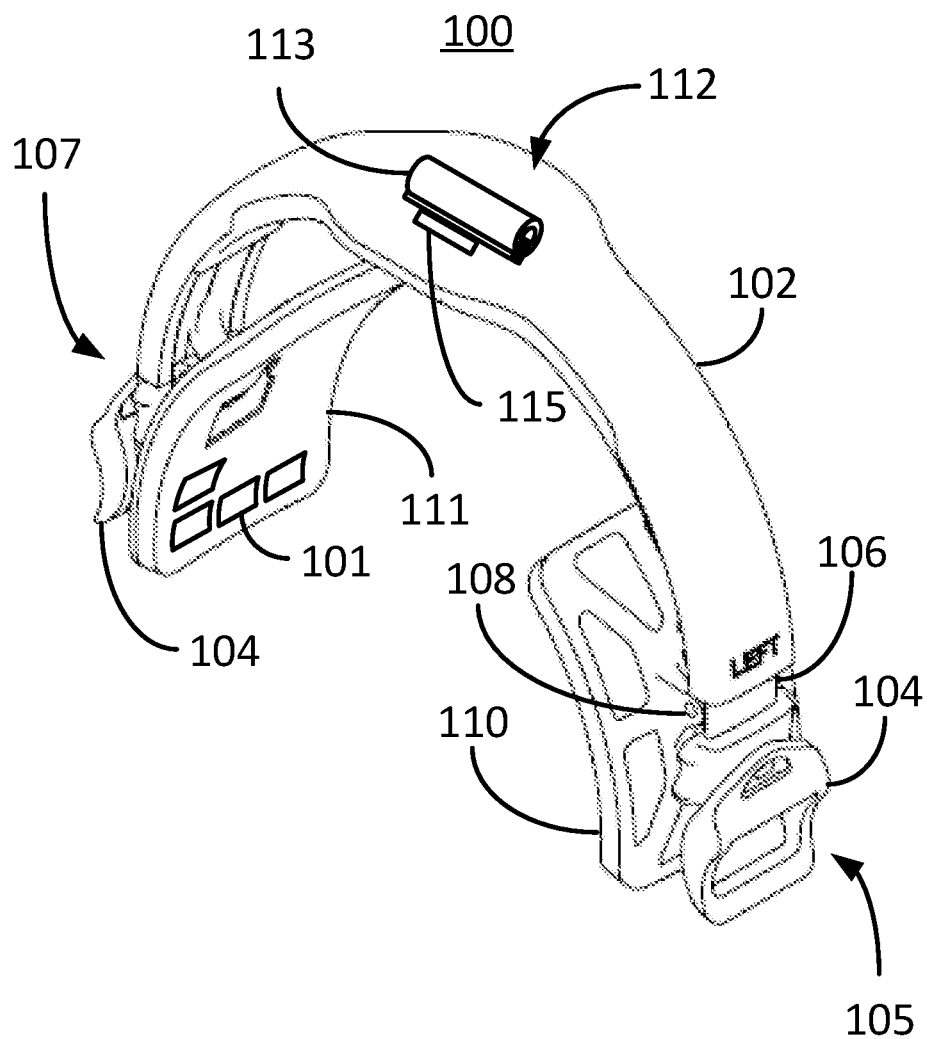
FIG. 1 depicts a ¾ view of an embodiment of an electrode holding headset in accordance with embodiments of the present invention.

To illustrate an exemplary environment in which preferred embodiments of the present invention can be practiced, FIG. 1 depicts a ¾ view of an embodiment of an electrode holding headset 100 in accordance with embodiments of the present invention. As shown, the headset/headband 100 defines a first end 105 and a second end 107 and conforms at least partially to a human skull. The first end 105 and the second end 107 provides spring load force against the human skull. A left electrode supporting panel 110 and a right electrode supporting panel 111 are pivotally attached to the headset 100 at pivot locations 108 essentially at the first and second ends. This embodiment depicts the electrode supporting panels 110 and 111 as curved to conform to the shape of a human head/skull, not shown. The headband 102 is a semi-rigid curved member that spring loads the electrode supporting panels 110 and 111 against a wearer's scalp, skull, or other parts of their head. Certain embodiments contemplate the electrodes 110 and 111 positioned just above the ears (not shown) of the wearer (on a human skull). The headband 102 is adjustable along varied circumferences of a head or head sizes via extension members 106. Locking members 104 lock the extension members 106 in place when the desired location of the electrode supporting panels 110 and 111 are found. The headband 102 provides a wider headband region 112 that rests over the apex of a skull for comfort and stability.

In this embodiment, power is provided to the electrodes 101 via a battery 113 disposed on the outer portion of the wider headband region 112 to actively sense or provide electrical or electromagnetic current to the brain. Certain embodiments contemplate battery power and wireless transmitting device 115 (via a transmitter, controller, memory,) adapted to transmit stimulating input to the brain/skull or receive sensing output from the brain/skull that is then sent to a wirelessly connected computer hub, not shown. Other embodiments contemplate one or more wireline's running along the headset 100 and connected to the electrodes. The wireline adapted to transmit stimulating input to the brain/skull or receive sensing output from the brain/skull to a physically connected computer hub.

Figure 2:
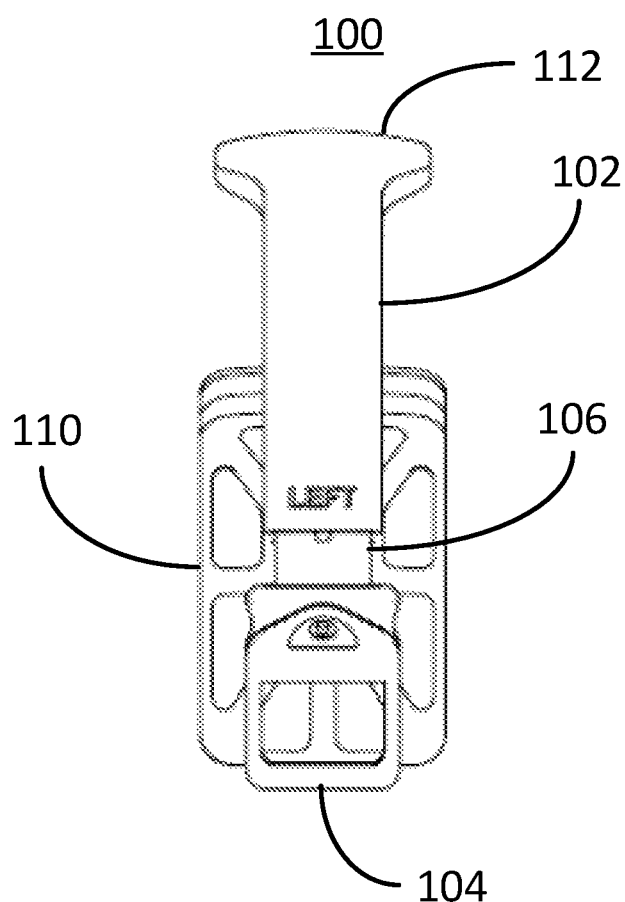
FIG. 2 illustratively shows a side view of the embodiment depicted in FIG. 1 consistent with embodiments of the present invention.

FIG. 2 illustratively shows a side view of the electrode supporting headset 100 depicted in FIG. 1 without the battery and wireless device consistent with embodiments of the present invention. The left side is displayed showing the wider headband region 112 that rests over the apex of a skull that narrows to the spring-loaded headband 102. As discussed above, the headband is extendable via an extension member 106 and locked into place via a locking member 104. The left electrode supporting panel 110 is shown for reference.

Figure 3:
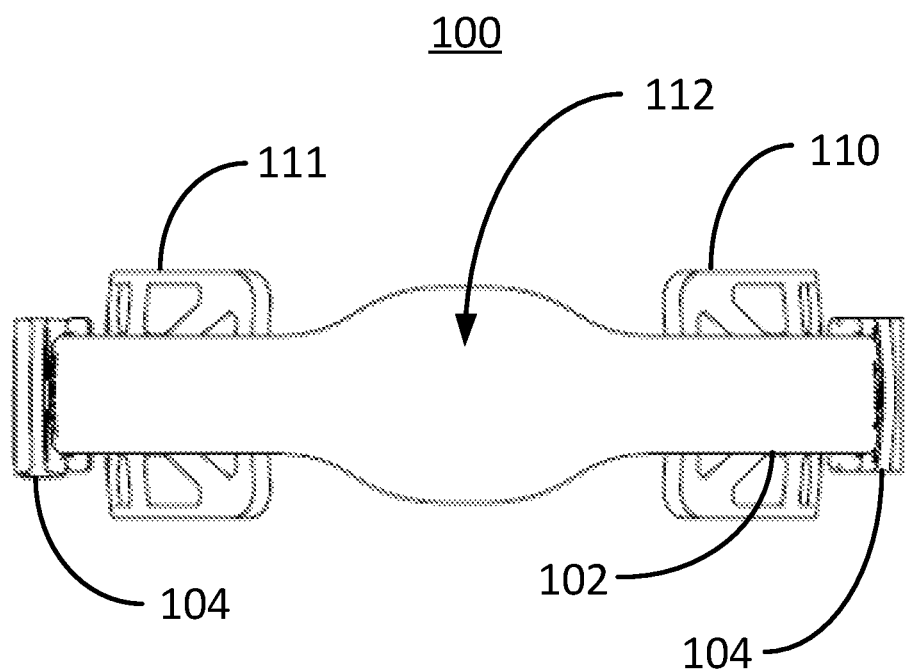
FIG. 3 illustratively shows a top view of the embodiment depicted in FIG. 1 consistent with embodiments of the present invention.

FIG. 3 depicts the top view of the electrode holding headset 100 without the battery and wireless device consistent with embodiments of the present invention. Prominently shown in the middle of the headset 102 is the wider headband region 112 that rest of the apex of the skull. The left electrode supporting panel 110, the right electrode supporting panel 111 and the two locking members 104 are shown from the top view.

Figure 4:
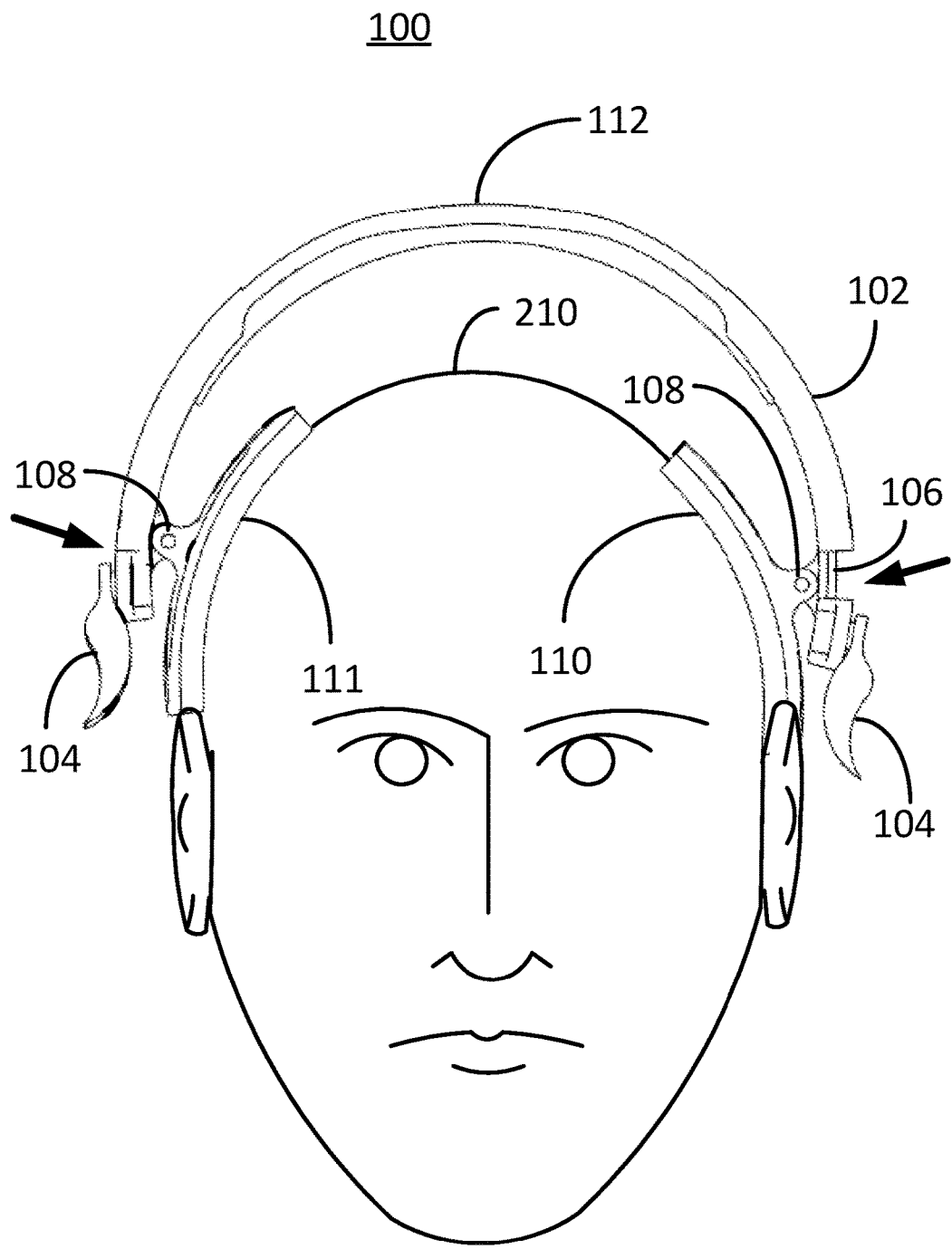
FIG. 4 illustratively depicts a front view of the embodiment depicted in FIG. 1 cooperating with the human skull consistent with embodiments of the present invention.

FIG. 4 illustratively depicts a front view of the embodiment depicted in FIG. 1 without the battery and wireless device cooperating with the human skull 210 consistent with embodiments of the present invention. The electrode holding headset 100 is shown cooperating with the human skull 210. As illustratively shown, the electrode supporting panels 110 and 111 are spring-loaded against the human skull 210 as shown by the arrows pointing towards the center of the human skull 210. The electrode supporting panels 110 and 111 are adapted to pivot about pivot points 108 to conform to the human skull 210. The extension member 106 is shown partially extended with the locking members 104 engaged (pointing down) to lock the extension members 106 in position.

Embodiments of the present invention contemplate one or more electrodes located on one or more of the electrode supporting panels 110 and 111. Embodiments contemplate that the electrodes can be active or passive electrodes that can be placed on the scalp, ear, forehead, or other reasonable places on a human head. A passive system is envisioned to hold a plurality of electrodes in place on the scalp, ear or forehead, for example, to passively detect current from the brain either which itself can be active, quiet or experiencing induced input such as auditory, visual, tactile as well as other energy sources, such as photon or chemical modulation. Certain embodiments contemplate active electrodes adapted to either stimulate the scalp or brain using a variety of forms of electrical or electromagnetic current in varied frequencies and frequency profiles (e.g. waveforms, signal intensity/amplitude, etc. Direct Current can be continuous or interrupted. Stimulation can also be alternating current called TES or Transcranial Electrical Stimulation and there is Transcranial Magnetic Stimulation—all working on the brain, placed in the appropriate locations over various parts of the brain. Embodiments of a passive electrode system envision a plurality of electrodes in place on the scalp, ear, forehead, or other regional places on human head to passively detect current from the brain either which itself can be active, quiet, or experiencing induced input such as auditory, visual, tactile as well as other energy sources such as photon or chemical modulation.

Embodiments contemplate the electrode holding headset 100 applied to the lateral sides of a human skull 210 in contact with the scalp above the ear using and attachment system for the frontal plane over the top of the skull 210 or secondarily posterior, inferior or anterior and a combination thereof, for example. While other embodiments contemplate the electrodes contacting the ears via the panels.

Figure 5:
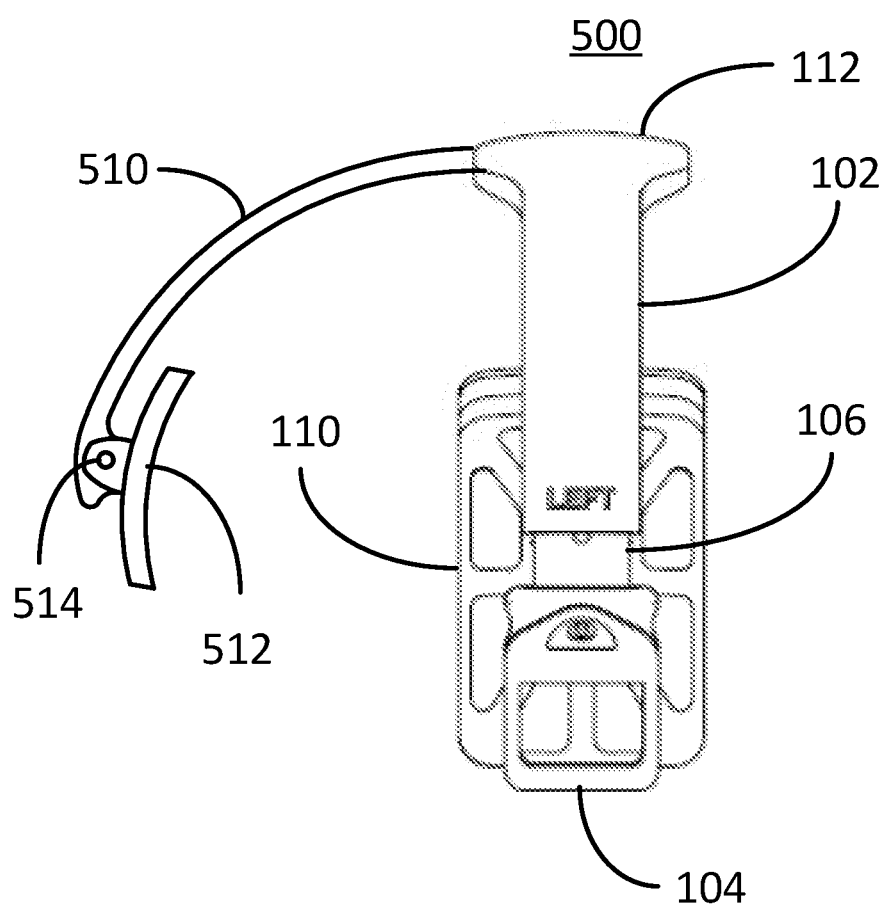
FIG. 5 illustratively depicts a side view of an electrode holding headset with an extending electrode supporting panel consistent with embodiments of the present invention.

Certain embodiments contemplate one or more electrodes integrated with the left electrode supporting panel 110 providing a reverse polarity to the one or more electrodes integrated with the right electrode supporting panel 111. In other words, the electrodes on the left electrode supporting panel 110 possesses an opposite polarity to the right electrode supporting panel 111. Other embodiments contemplate one or more electrodes of opposite polarity over the frontal scalp or forehead relative to paired electrodes (one or more) in contact with another port of the scalp, skull, or over a body part on the other side or even ipsilateral side of the body. This embodiment could include one electrode held in place with the electrode supporting headset 100 over the frontal scalp and/or forehead and the opposite electrode over the contralateral scalp overlying the frontal motor, sensory, temporal or parietal regions of the brain (see FIG. 5). The contralateral or opposite polarity electrode could also be over the opposite side of the neck, upper back or in some cases further down the body on either side.

Certain embodiments contemplate one electrode or set of electrodes on the scalp and the other electrode on the neck or upper neck of the person. This can be accomplished by extending an arm 510 from the electrode supporting headset 500. Such as that depicted in capital FIG. 5 which illustratively depicts an electrode supporting headset 500 with an arm 510 extending from the wider headband region 112. The arm 510 possesses a pivotable electrode supporting panel 512 (pivotable about pivot point 514) that conforms to the forehead or neck of a person using the elector supporting headset 500. Other embodiments contemplate at least one other electrode attached to the human body and connected to the headset 100.

Embodiments of the electrode supporting headsets 100 and 500 contemplate the headset being capable and adapted to be self-administered with only one hand. In other words, a user (or person using) electrode supporting headsets can put the electrode supporting headset on their head and adjust the electrode supporting panels to be placed in the appropriate parts of their skull, forehead, neck, or upper body with one hand.

Embodiments of the electrode supporting headset 100 contemplates supporting a small magnetic coil (not shown) to stimulate the brain, such as a transcranial magnetic stimulator.

Figure 6:
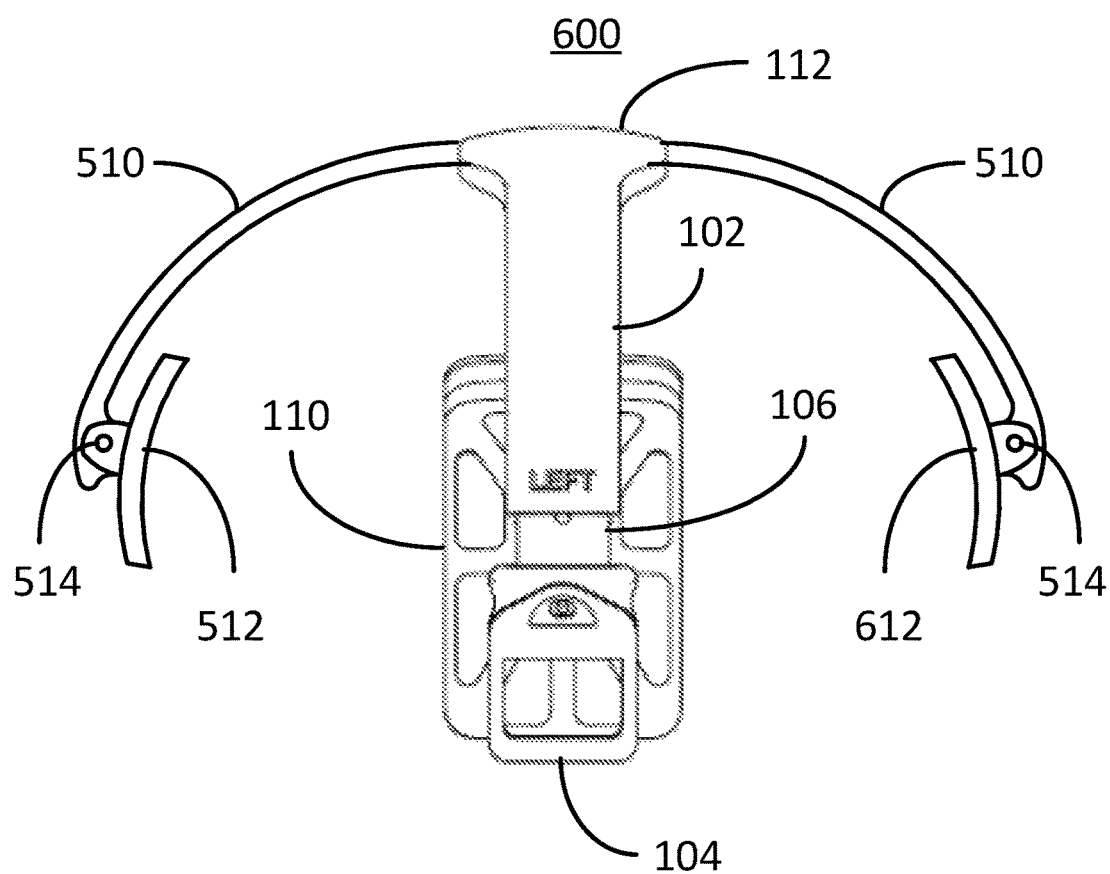
FIG. 6 illustratively depicts a side view of an electrode holding headset with a pair of extending electrode supporting panels consistent with embodiments of the present invention.

Other embodiments contemplate a first electrode supporting panel possessing a plurality of electrodes with a relatively negative charge thereon and a second electrode supporting panel possessing a plurality of electrodes with a relatively positive charge thereon. Optionally, a first electrode supporting panel is envisioned to possess a plurality of electrodes with a negative charge thereon in contact with a person forehead while a second electrode supporting panel 612 possessing a plurality of electrodes with positive charge thereon on the opposite side of the scalp near or over the occipital portion of the skull (overlaying the frontal motor, sensory, temp oral or parietal regions of the brain), FIG. 6, or over an ipsilateral part of the body (in the same line with the occipital portion along the person's neck or back) or even ipsilateral side of the body.

Figure 7:
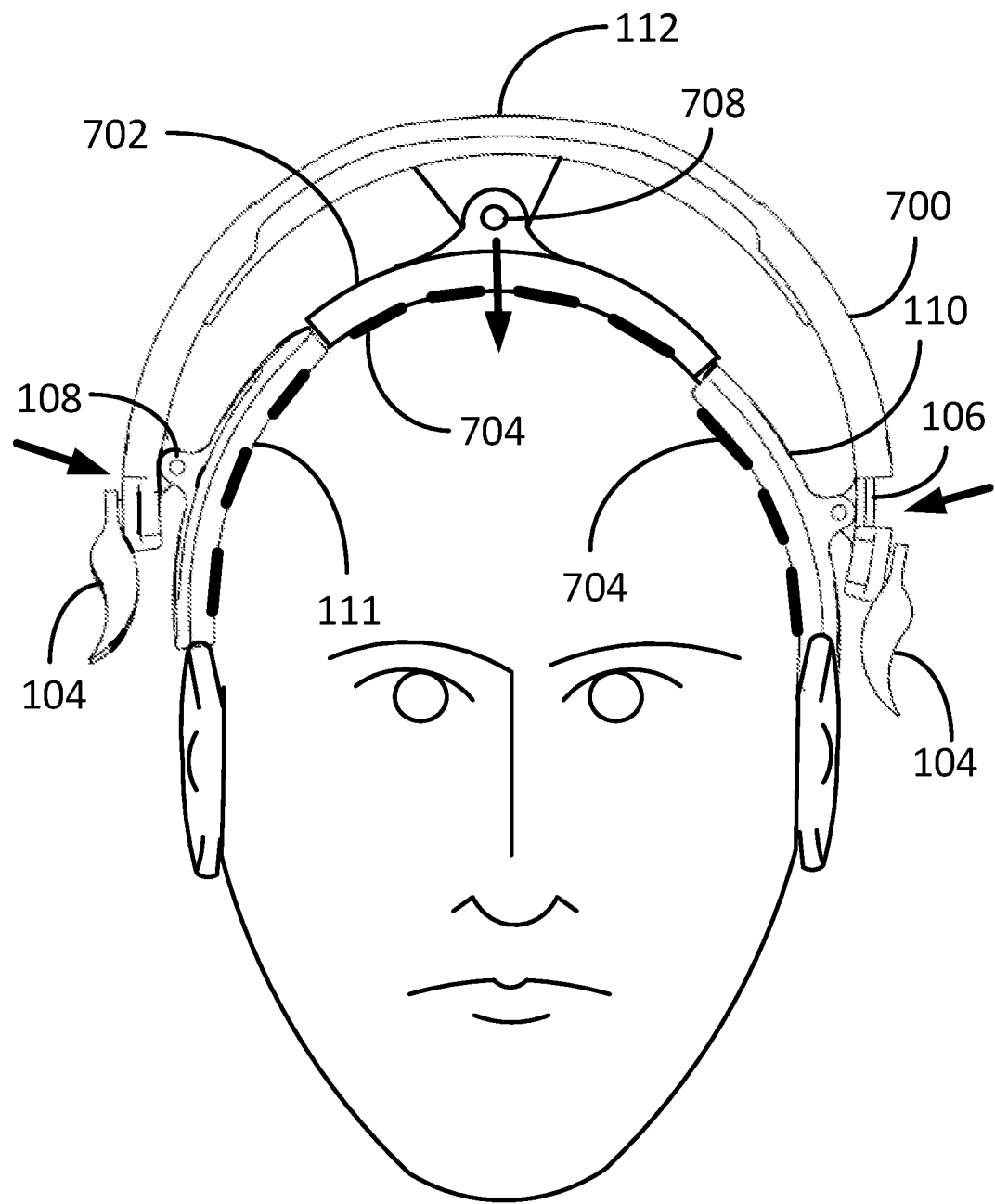
FIG. 7 illustratively depicts a front view of a headset embodiment cooperating with the human skull consistent with embodiments of the present invention.

FIG. 7 shows yet another embodiment illustrating a plurality of electrodes 704 disposed along a semi-rigid curved headset 700. Here, there is a top panel 702 that is pivotally adjustable about a pivot point 708 over the top of a human skull. The arrows indicate the pressure direction of the panels 110, 111 and 702 over the human head. An optional embodiment contemplates more panels, less panels or no panels with the electrodes traversing the curved headset 700 adapted to contact a human skull. In this arrangement, the electrodes 704 contact the human head along the path of the headset 700 from the left ear to the right ear.

Certain embodiments contemplate a plurality of electrodes that contact a human skull via the headset 100 or 700. The plurality of electrodes includes a first group of electrodes and a second group of electrodes. The first group of electrodes possessing a negative polarity charge and the second group possessing positive polarity, relative to the first group.

A method for using the headset 100 is further contemplated whereby the headset, as previously discussed, is semi-rigid with a curvature smaller than a human skull, the headset having a first end supporting a first electrode arrangement and a second end supporting a second electrode arrangement. A person will bend the headset in an open direction by spacing apart the first end 105 from the second end 107 in a direction that opens up the curvature of the headset 100. While in the open position, place the headset 100 over the human skull while the headset is spaced apart. In this way, the curvature of the headset is a bit greater than the human skull allowing the panels 110 and 111 to unobstructively be placed over the skull. When in position over the skull, release the headset 100 allowing the first electrode arrangement and the second electrode arrangement to move towards one another in a closed position that compresses the electrodes against the human skull. The first electrode arrangement on a first panel 110 and the second electrode arrangement on a second panel 111, the panels pivoting to conform to the human skull. Positioning the first electrode arrangement on the human skull above a left ear and the second electrode arrangement on the human skull above a right ear is done to place the electrodes in the right positions over the brain. The panels 110 and 111 can then be locked into position with the latches 104. The electrodes can be dampened to improve contact with the human head, the electrodes can protrude to penetrate through hair on the head, or can have adhesive if the head is shaved. When the electrodes are in contact and pressing against the skin of the person's head, the electrodes can be energized via a power supply (wireline or via a battery) to produce stimulation or to receive signals from the brain. Some embodiments contemplate passively sensing signals from the brain by the energy produced by the brain transmitted through the skull.

It is to be understood that even though numerous characteristics and advantages of various embodiments of the present invention have been set forth in the foregoing description, together with the details of the structure and function of various embodiments of the invention, this disclosure is illustrative only, and changes may be made in detail, especially in matters of structure and arrangement of parts within the principles of the present invention to the full extent indicated by the broad general meaning of the terms in which the summary is expressed. For example, additional electrode supporting panels can be used in a consistent manner with embodiments of the present invention while still maintaining substantially the same functionality without departing from the scope and spirit of the present invention. Another example can include various linked arms with electrode supporting panels were multiple electrode supporting panels along a single arm, or various lines emanating from the headset/headband that can adhere to various parts of the body without departing from the scope and spirit of the present invention.

It will be clear that the present invention is well adapted to attain the ends and advantages mentioned as well as those inherent therein. While presently preferred embodiments have been described for purposes of this disclosure, numerous changes may be made which readily suggest themselves to those skilled in the art and which are encompassed in the spirit of the invention disclosed and presented in the appended claims.

What is claimed is:

1. An electrode holding device comprising:
  a semi-rigid curved headset having a first end and a second end adapted to conform at least partially to a human skull and to provide spring load force against the human skull at the first and the second ends;
a first electrode panel adapted to conform to a first portion of the human skull attached to the first end of the headset;
a second electrode panel adapted to conform to a second portion of the human skull attached to the second end of the headset;
the first electrode panel adapted to pivot about a first pivot point and the second electrode panel adapted to pivot about a second pivot point;
a first electrode disposed in a first position on the first electrode panel arranged to contact at least part of the first portion of the human skull under pressure from the spring load force;
a second electrode disposed in a second position on the second electrode panel arranged to contact at least part of the second portion of the human skull under the pressure from the spring load force; and
a first group of electrodes and a second group of electrodes attached to the headset, the first group of electrodes and the second group of electrodes are adapted to contact the human skull, the first group of electrodes and the second group of electrodes disposed along a same path as the semi-rigid curved headset.

2. The electrode holding device of claim 1 further comprising an arm that extends from the headset, at least a third electrode disposed on a distal end of the arm that is adapted to be spring-loaded against a forehead of the human skull.

3. The electrode holding device of claim 1 wherein one of the first group of electrodes or the second group of electrodes possesses a polarity and is adapted to be in contact with a first side of the skull while the rest of the electrodes possess a reverse polarity and are adapted to be in contact with the opposite side of the skull.

4. The electrode holding device of claim 1 further comprising an arm that extends from the headset, at least a third electrode disposed on a distal end of the arm that is adapted to be spring-loaded against a human neck.

5. The electrode holding device of claim 1 wherein the electrodes are stimulating electrodes, sensing electrodes, or both stimulating and sensing electrodes.

6. The electrode holding device of claim 1 wherein the first electrode panel is adapted to be in contact under pressure with the human skull above a left ear at the first end and the second electrode panel is adapted to be in contact under pressure with the human skull above a right ear at the second end, the first end and the second end are is contact under the pressure from the spring load force.

7. The electrode holding device of claim 1 wherein the first electrode panel and the second electrode panel are adjustable along the semi-rigid curved headset to contact different regions of the human skull.

8. The electrode holding device of claim 1 wherein the first electrode possesses a negative polarity relative to the second electrode.

9. The electrode holding device of claim 1 further comprising a third electrode panel adapted to conform to a human skull apex attached to the headset, the third electrode panel having at least a third electrode panel electrode.

10. The electrode holding device of claim 1 wherein the first and the second panels are adapted to be mechanically locked into position on the human skull via a locking mechanism linked directly to the curved headset.

11. A method for using an electrode holding device comprising:
providing a headset that is semi-rigid with a curvature smaller than a human skull, the headset having a first end supporting a first electrode arrangement possessing a plurality of first electrodes and a second end supporting a second electrode arrangement possessing a plurality of second electrodes;
bending the headset in an open direction by spacing apart the first end from the second end;
placing the headset over the human skull while the headset is spaced apart;
releasing the headset while over the human skull allowing the first electrode arrangement and the second electrode arrangement to move towards one another in a closed position that compresses the first and the second electrode arrangements against the human skull, the first electrode arrangement on a first panel and the second electrode arrangement on a second panel, the panels pivoting to conform to the human skull;
positioning the first electrode arrangement on the human skull just above a left ear and the second electrode arrangement on the human skull just above a right ear, with the headset passing over the apex of the human skull the first electrode arrangement and the second electrode arrangement are essentially in-line with the headset as viewed laterally on the human skull; and
energizing the first electrode arrangement and the second electrode arrangement while in contact with the human skull.

12. The method of claim 11 further comprising sensing electrical activity through the first electrode arrangement and the second electrode arrangement.

13. The method of claim 11 wherein the energizing can be accomplished passively via energy generated from the human skull or actively via energy from a power supply.

14. The method of claim 11 further comprising providing at least one arm that extends from the headset, at least a third electrode arrangement disposed on a distal end of the arm, contacting the third electrode arrangement on a forehead of the human skull.

15. An electrode holding device comprising:
a headset having a neutral curvature with a radius smaller than a human skull, the headset possessing a first end and a second end adapted to conform at least partially to a human skull; the headset adapted to provide spring load force against the human skull at the first and the second ends;
a first electrode panel adapted to conform to a first portion of the human skull attached to the first end of the headset just above and practically touching a left ear of the human skull;
a second electrode panel adapted to conform to a second portion of the human skull attached to the second end of the headset just above and practically touching a right ear of the human skull;
the first electrode panel and the second electrode panel are adapted to contact the lateral sides of the human skull along a common path with the headset, the headset arranged to pass through the apex of the human skull;
the first electrode panel adapted to pivot about a first pivot point and the second electrode panel adapted to pivot about a second pivot point;
a first electrode assembly possessing a first group of electrodes comprised by the first electrode panel arranged to contact at least part of the first portion of the human skull under pressure from spring load force generated from the headset bent beyond the neutral curvature;

a second electrode assembly possessing a second group of electrodes disposed in a second position on the second electrode panel arranged to contact at least part of the second portion of the human skull under the pressure from the spring load force.

* * * * *